US006955685B2

(12) United States Patent
Escamilla et al.

(10) Patent No.: US 6,955,685 B2
(45) Date of Patent: Oct. 18, 2005

(54) EXPANDABLE STENT WITH RADIOPAQUE MARKERS AND STENT DELIVERY SYSTEM

(75) Inventors: Angeli Escamilla, Miramar, FL (US); Donald K. Jones, Lauderhill, FL (US); Vladimir Mitelberg, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 279 days.

(21) Appl. No.: 10/608,659

(22) Filed: Jun. 27, 2003

(65) Prior Publication Data
US 2004/0078071 A1 Apr. 22, 2004

Related U.S. Application Data

(63) Continuation-in-part of application No. 10/365,282, filed on Feb. 12, 2003.
(60) Provisional application No. 60/412,867, filed on Sep. 23, 2002.

(51) Int. Cl.[7] .................................................. A61F 2/06
(52) U.S. Cl. ...................... 623/1.12; 623/1.34; 606/200
(58) Field of Search .............................. 623/1.11, 1.12, 623/1.23, 1.34; 606/108, 153, 154, 155, 156, 606/200

(56) References Cited

U.S. PATENT DOCUMENTS

| 4,768,507 | A | 9/1988 | Fischell et al. |
|---|---|---|---|
| 5,288,711 | A | 2/1994 | Mitchell et al. |
| 5,516,781 | A | 5/1996 | Morris et al. |
| 5,563,146 | A | 10/1996 | Morris et al. |
| 5,646,160 | A | 7/1997 | Morris et al. |
| 5,741,327 | A | 4/1998 | Frantzen |
| 6,126,685 | A | 10/2000 | Lenker et al. |
| 6,214,036 | B1 | 4/2001 | Letendre et al. |
| 6,231,598 | B1 | 5/2001 | Berry et al. |
| 6,302,893 | B1 | 10/2001 | Limon et al. |
| 6,334,871 | B1 | 1/2002 | Dor et al. |
| 6,361,558 | B1 | 3/2002 | Hieshima et al. |
| 6,395,017 | B1 | 5/2002 | Dwyer et al. |
| 6,482,227 | B1 * | 11/2002 | Solovay ..................... 623/1.13 |
| 2001/0027339 | A1 | 10/2001 | Boatman et al. |
| 2002/0055767 | A1 | 5/2002 | Forde et al. |
| 2002/0082683 | A1 | 6/2002 | Stinson et al. |

(Continued)

FOREIGN PATENT DOCUMENTS

EP        1 036 550 A2    9/2000

(Continued)

OTHER PUBLICATIONS

European Search Report EP.03 25 5883 dated Nov. 20, 2003 with Annex to the European Search Report.

(Continued)

Primary Examiner—Corrine McDermott
Assistant Examiner—Thomas J Sweet
(74) Attorney, Agent, or Firm—Henry W. Collins

(57) ABSTRACT

An expandable stent and delivery system therefor is provided for treating vascular diseases such as partially occluded blood vessels and aneurysms. The delivery system includes proximal, intermediate and distal cylindrical members disposed about an elongated core member. The proximal, intermediate, and distal cylindrical members are spaced apart such that first and second gaps are formed. The expandable stent includes anchor members which are formed by winding a radiopaque coil onto a threaded portion of a strut member of the expandable stent. The expandable stent is mounted on the intermediate cylindrical member with the anchor members disposed within the gaps between the cylindrical members. A deployment catheter is used to compress and constrain the stent about the intermediate cylindrical member to thereby interlock the stent onto the core member.

42 Claims, 13 Drawing Sheets

U.S. PATENT DOCUMENTS

2002/0193862 A1   12/2002   Mitelberg et al.
2002/0193868 A1   12/2002   Mitelberg et al.

FOREIGN PATENT DOCUMENTS

| EP | 1 157 683 A2 | 11/2000 |
| EP | 1 374 801 A1 | 1/2004 |
| WO | WO 00/71058 A1 | 11/2000 |
| WO | WO 00/76424 A1 | 12/2000 |
| WO | WO 02/06778 A2 | 9/2002 |

OTHER PUBLICATIONS

European Patent Office Communication for European Patent Application No. 03255883.5 (Examination Report) dated Nov. 8, 2004.

\* cited by examiner

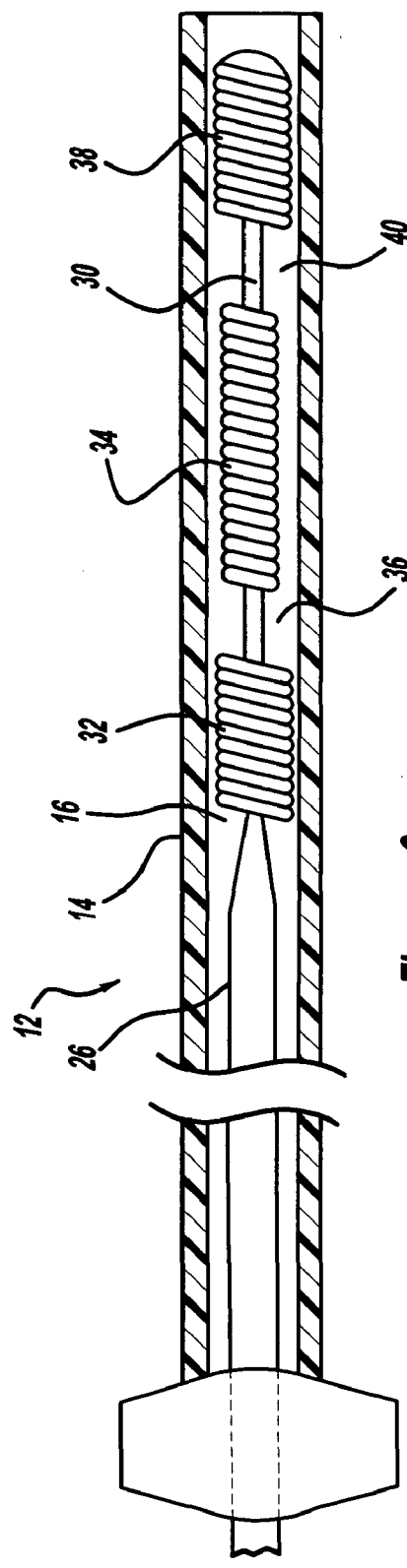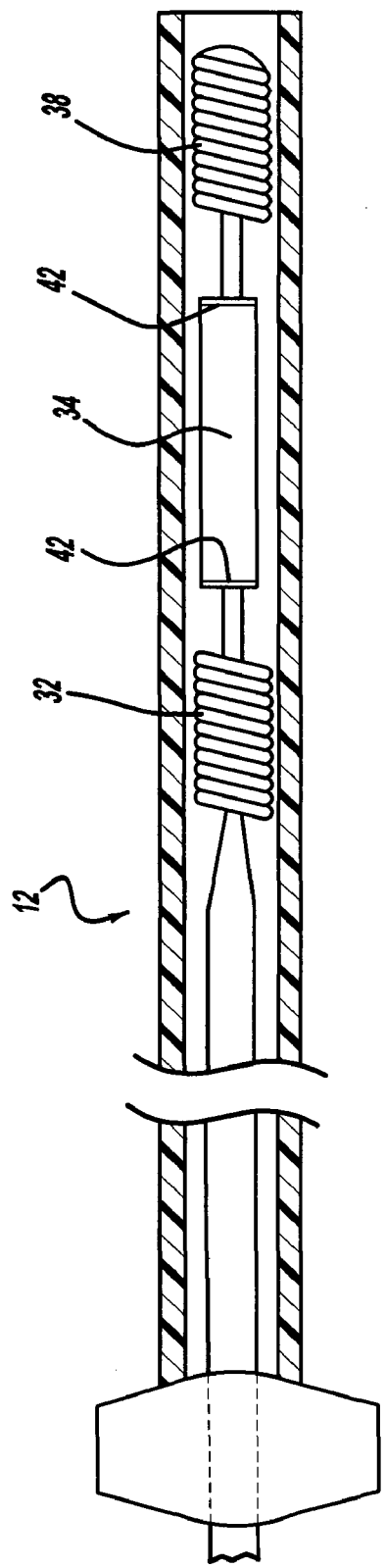

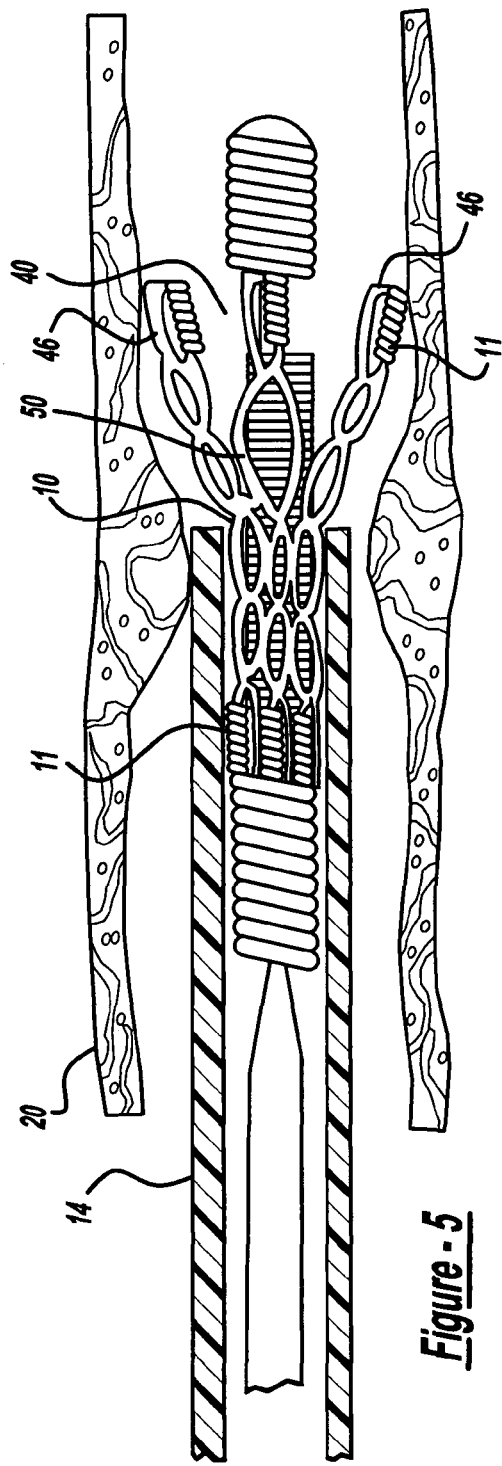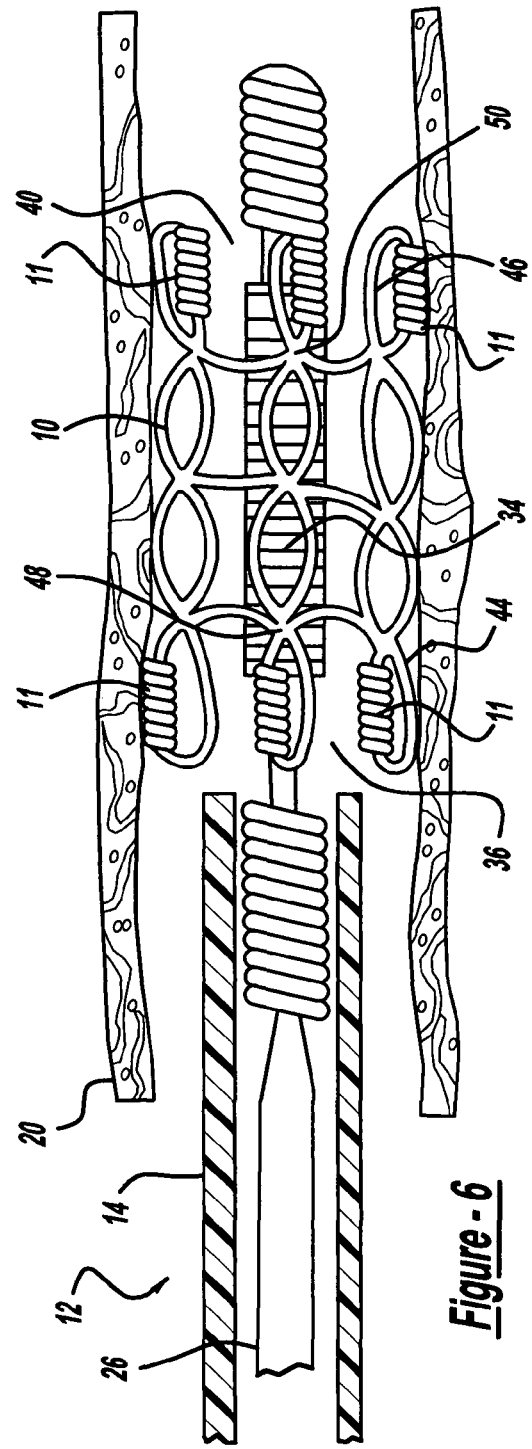

EXPANDABLE STENT WITH RADIOPAQUE MARKERS AND STENT DELIVERY SYSTEM

Continuation-in-Part (CIP) of prior application Ser. No: 10/365,282, filed on Feb. 12, 2003, which is a nonprovisional of U.S. patent application Ser. No. 60/412,867, filed on Sep. 23, 2002.

BACKGROUND OF THE INVENTION

1. Field of the Invention

The disclosed invention relates to intravascular therapeutic devices and delivery systems therefor, and more particularly, to expandable stents and delivery systems which may be used in the treatment of blood vessel disorders. More specifically, this invention relates to extremely small expandable stents and delivery systems used to treat partially occluded blood vessels, or aneurysms, within the brain.

2. Description of the Prior Art

On a worldwide basis, nearly one million balloon angioplasties are performed annually to treat vascular diseases such as blood vessels that are clogged or narrowed by a lesion or stenosis. The objective of this procedure is to increase the inner diameter of the partially occluded blood vessel lumen. In an effort to prevent restenosis without requiring surgery, short flexible cylinders or scaffolds, referred to as stents, are often placed into the blood vessel at the site of the stenosis. Stents are typically made of metal or polymers and are widely used for reinforcing diseased blood vessels. Stents are also useful in treating aneurysms by providing an internal lumen to cover an aneurysm and thus reduce the flow of blood and the pressure within the aneurysm.

Some stents are expanded to their proper size using a balloon catheter. Such stents are referred to as "balloon expandable" stents. Other stents, referred to as "self-expanding" stents, are designed to elastically resist compression in a self-expanding manner. Balloon expandable stents and self-expanding stents are compressed into a small diameter cylindrical form and deployed within a blood vessel using a catheter-based delivery system.

Recently, stents have been developed with radiopaque markers to aid in the visualization of the stent upon deployment. Radiopaque markers facilitate the positioning of the stent within a blood vessel by allowing a physician to determine the exact location, size, and orientation of the stent under x-ray or fluoroscopy. These markers are typically formed of a radiopaque material such as tantalum, zirconium, titanium, or platinum. Published U.S. Patent Application No. 2002/0082683 entitled, "Radiopaque Markers For Implantable Prosthesis," discloses one such radiopaque marker comprised of a pigtail, knot, or ring, of tantalum wire wrapped around a crossing point of struts within a stent.

SUMMARY OF THE INVENTION

In accordance with one aspect of the present invention, there is provided an expandable stent and delivery system. The delivery system includes an elongated core member having proximal and distal cylindrical members disposed about the distal portion of the elongated core member. The distal cylindrical member is generally positioned distally from the proximal cylindrical member. The proximal and distal cylindrical members are spaced apart to define a gap. The expandable stent is comprised of a small diameter, thin walled, skeletal tubular member. The wall of the tubular member is cut to define a plurality of cells which are formed by a plurality of interconnected strut members. One of the strut members is formed with a threaded portion on the strut member. A coil comprised of radiopaque material is wound onto the threaded portion of the strut member to thereby define an anchor member which also serves as a radiopaque marker. The anchor member has a longitudinal length slightly shorter than the longitudinal length of the gap. The expandable stent is mounted on at least one of the cylindrical members of the delivery system and is positioned such that the anchor member is interlocked within the gap. The elongated core member and stent are carried by a deployment catheter which compresses the expandable stent about one of the cylindrical members thereby causing the anchor member to be retained in the gap. With this arrangement, the expandable stent is locked onto the elongated core member until such time as the deployment catheter is withdrawn thereby permitting the stent to expand.

In accordance with another aspect of the present invention, the expandable stent includes a plurality of strut members formed with threaded portions on the strut members. A coil comprised of radiopaque material is wound onto the threaded portion of each of the strut members to thereby define anchor members which also serve as radiopaque markers. The anchor members are preferably positioned within the distal and/or proximal section of the expandable stent.

In accordance with still another aspect of the present invention, the expandable stent includes a flared proximal section and a flared distal section with outer diameters of the flared sections being greater than the outer diameter of the central section of the stent. The flared proximal section and flared distal section have outer diameters up to, or approximately equal to, three times the outer diameter of the central section of the stent.

In accordance with yet another aspect of the present invention, the expandable stent includes a strut member with threads cut into an edge of the strut member. Alternatively, the strut member may include threads which are cut into opposing edges of the strut member. The coil of radiopaque material is then wound onto the opposing threads of the strut member to serve as the anchor member. In addition, the expandable stent may further include multiple such anchor members.

BRIEF DESCRIPTION OF THE DRAWINGS

FIG. 2 is an enlarged partial sectional view of the delivery system of FIG. 1 with an intermediate cylindrical member which takes the form of a helically wound flexible coil;

FIG. 3 is an enlarged partial sectional view of the delivery system of FIG. 1 with an intermediate cylindrical member which takes the form of a flexible cylindrical sleeve;

FIG. 5 is an enlarged partial sectional view of the delivery system with the deployment catheter moved proximally, allowing the distal section of the expandable stent to expand within the blood vessel while the proximal section of the expandable stent remains interlocked within the deployment catheter;

FIG. 6 is an enlarged sectional view of the delivery system with the deployment catheter moved proximally and the expandable stent fully expanded within the blood vessel;

DESCRIPTION OF THE PREFERRED EMBODIMENT

Figure 1:
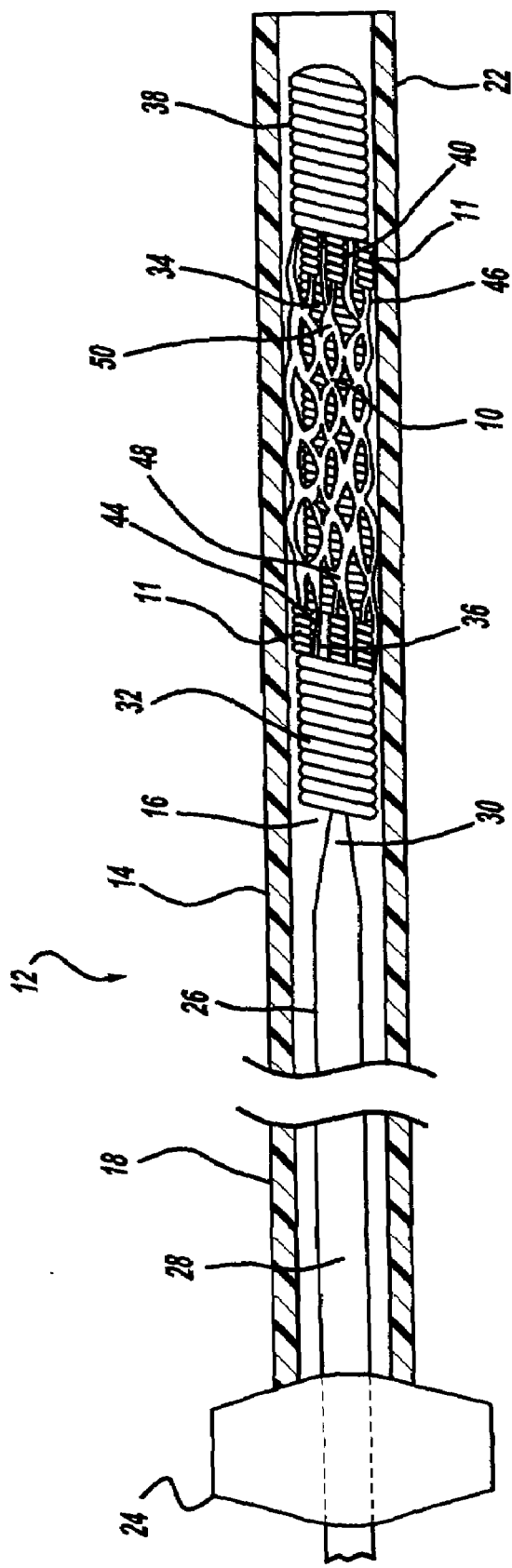
FIG. 1 is an enlarged partial sectional view of an expandable stent with anchor members and a delivery system therefor in accordance with the preferred embodiment of the present invention.

FIG. 1 illustrates an expandable stent 10 and delivery system 12. The delivery system 12 includes a deployment catheter 14 which takes the form of an elongated tube having a lumen 16. Preferably, the proximal section 18 of the deployment catheter 14 is formed of a nylon material having a durometer in the range of about 60 D to 75 D. The proximal section 18 of the deployment catheter 14 is sufficiently flexible to traverse a blood vessel, but is sufficiently rigid so that it can be pushed distally through the blood vessel. The distal section 22 of the deployment catheter 14 is preferably formed of a pellethane material having a durometer of between 25 D and 55 D.

A winged hub 24 is coupled to the proximal section 18 of the deployment catheter 14. Formed from a polymer material, the winged hub 24 is used to insert the deployment catheter 14 into a blood vessel, such as a blood vessel within the brain of a patient. The delivery system 12 also includes an elongated core member 26 which is formed of wire, preferably nitinol, but may also be formed from other metal alloys or a polymer material. The core member 26 is slideably disposed within the lumen 16 of the deployment catheter 14 and is tapered so that the proximal portion 28 of the core member 26 is of a greater diameter than the distal portion 30 of the core member 26.

The delivery system 12 further includes a proximal cylindrical member 32 disposed about the distal portion 30 of the core member 26. Preferably, the proximal cylindrical member 32 is a helically wound flexible coil made of metal, but may alternatively be formed of a polymer material. An intermediate cylindrical member 34 (shown within the stent) is also disposed about the core member 26 and is generally positioned distally from the proximal cylindrical member 32. The intermediate cylindrical member 34 is spaced apart from the proximal cylindrical member 32 such that the space between the proximal and intermediate cylindrical members 32, 34 forms a first gap 36. The length of the first gap 36 may range from 0.019 inches to 0.19 inches, with a preferred length of 0.040 inches.

A distal cylindrical member 38 is disposed about the core member 26 and is generally positioned distally from the intermediate cylindrical member 34. The distal cylindrical member 38 is spaced apart from the intermediate cylindrical member 34 such that the space between the intermediate and distal cylindrical members 34, 38 forms a second gap 40. The length of the second gap 40 may range from about 0.019 inches to 0.19 inches, with a preferred length of 0.040 inches. Preferably, the distal cylindrical member 38 is a helically wound flexible coil made from metal, but may alternatively be formed of a polymer material. The delivery system 12 is described in more detail in U.S. patent application Ser. No. 10/365,282, entitled "Expandable Stent and Delivery System," filed on Feb. 12, 2003 (Attorney Docket No. CRD-5001-US-NP) and assigned to the same assignee as the present patent application.

Mounted on the intermediate cylindrical member 34, the expandable stent 10 may take on many different patterns or configurations. Examples of such stents are disclosed in U.S. patent application Ser. Nos. 10/163,116 and 10/163,248, both entitled "Intravascular Stent Device," both filed on Jun. 5, 2002 and assigned to the same assignee as the present patent application. Preferably, the stent 10 is coated with an agent, such as heparin or rapamycin, to prevent stenosis or restenosis of the vessel. Examples of such coatings are disclosed in U.S. Pat. Nos. 5,288,711; 5,516,781; 5,563,146 and 5,646,160.

The stent 10 is preferably laser cut from a tubular piece of nitinol to form a skeletal tubular member. The skeletal tubular member has a thin wall, a small diameter, and when cut forms a plurality of cells which are created by a plurality of interconnected strut members. The nitinol is treated so as to exhibit superelastic properties at body temperature. The stent 10 includes proximal and distal strut members 44, 46 coupled to the proximal and distal sections 48, 50 of the stent 10. Additionally, the stent 10 includes anchor members 11 positioned on the proximal strut members 44 and distal strut members 46 of the stent 10.

Figure 1A:
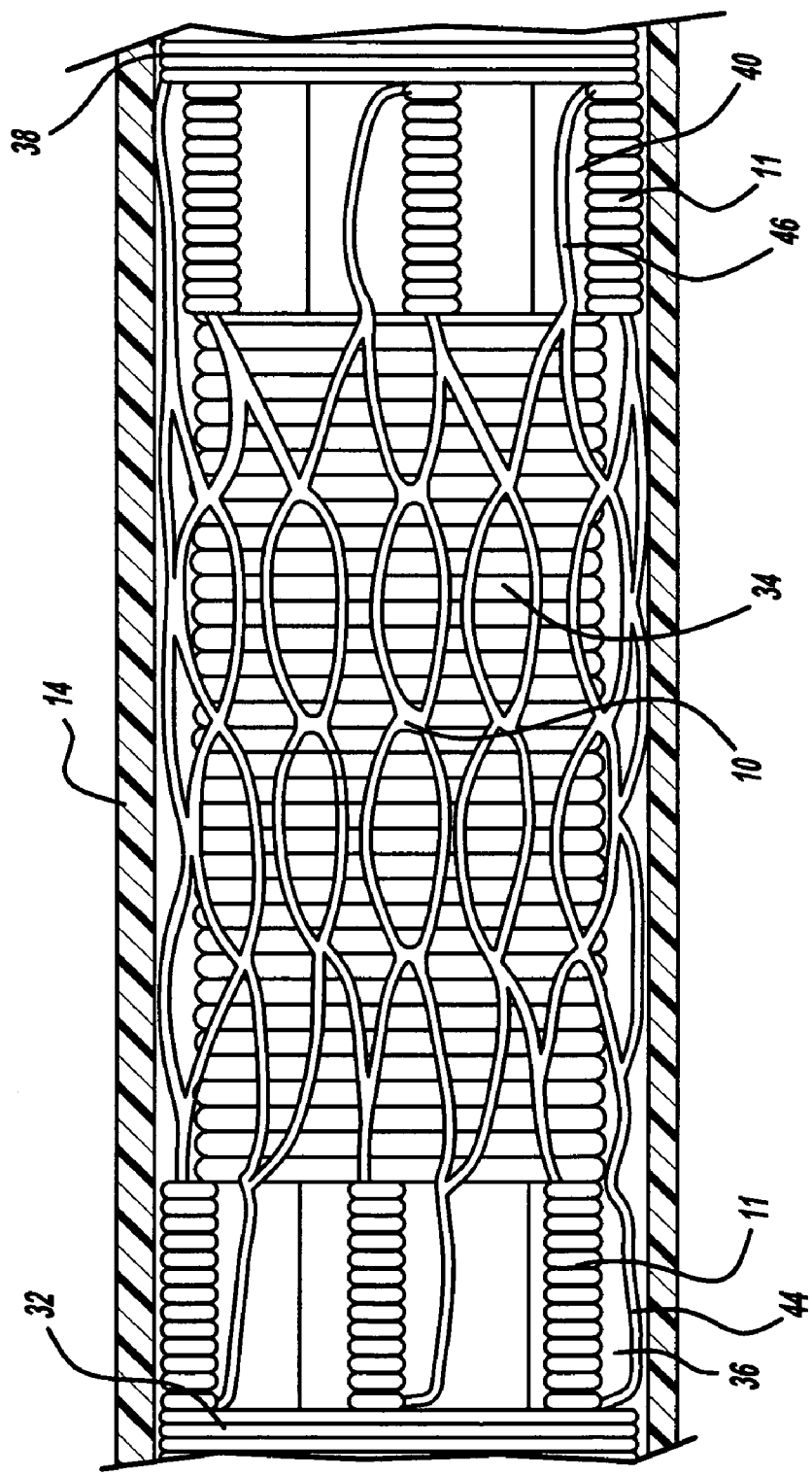
FIG. 1A is an enlarged partial sectional view of the expandable stent of FIG. 1 positioned within the delivery system.

FIG. 1A illustrates an enlarged view of the expandable stent 10 mounted on the intermediate cylindrical member 34. As the stent 10 is positioned and mounted on the intermediate cylindrical member 34, the anchor members 11 on the proximal strut members 44 align with and are disposed within the first gap 36, formed by the space between proximal cylindrical member 32 and intermediate cylindrical member 34. Similarly, the anchor members 11 on the distal strut members 46 align with and are disposed within the second gap 40, formed by the space between intermediate cylindrical member 34 and distal cylindrical member 38. In this configuration, the stent 10 is locked in place and may be pushed or pulled through the deployment catheter 14 without damaging or deforming the stent 10.

FIG. 2 illustrates the delivery system 12 without the expandable stent 10. The delivery system 12 includes an elongated core member 26 disposed within the lumen 16 of a deployment catheter 14. Proximal, intermediate and distal cylindrical members 32, 34 and 38 are disposed about the distal portion 30 of the core member 26. The first gap 36 is defined as the space between the proximal cylindrical member 32 and the intermediate cylindrical member 34. The second gap 40 is defined as the space between the intermediate cylindrical member 34 and the distal cylindrical member 38. In the embodiment shown in this figure, the intermediate cylindrical member 34 is a helically wound flexible coil. Preferably, the flexible coil is made of a metallic material and has a length less than the length of the stent 10. When the stent 10 is mounted on the intermediate cylindrical member 34, the stent is constrained about the intermediate cylindrical member and thus locked onto the core member 26 by the deployment catheter 14. In this configuration, the stent and delivery system 12 remain sufficiently flexible to traverse tortuous blood vessels within the brain.

FIG. 3 also shows the delivery system 12 without the expandable stent 10, however, in the embodiment shown in this figure, the intermediate cylindrical member 34 takes the form of a flexible cylindrical sleeve. Preferably, the cylindrical sleeve is made of a polymer material having a smooth outer surface. In this configuration, a stent with a drug coating may be mounted on the cylindrical sleeve and thereby protected from damage caused by friction between the stent and the intermediate cylindrical member 34.

Attached to the ends of the intermediate cylindrical member 34 are reinforcing members 42. The reinforcing members 42 take the form of metallic rings or disks, and alternatively may be made of a polymer material. Preferably, the reinforcing members 42 are made of the same material as the intermediate cylindrical member 34. The reinforcing members 42 provide support to the ends of the intermediate cylindrical member 34 so that the ends resist deformation. Reinforcing members 42 may alternatively be disposed on the ends of the proximal and distal cylindrical members 32, 38.

Figure 4:
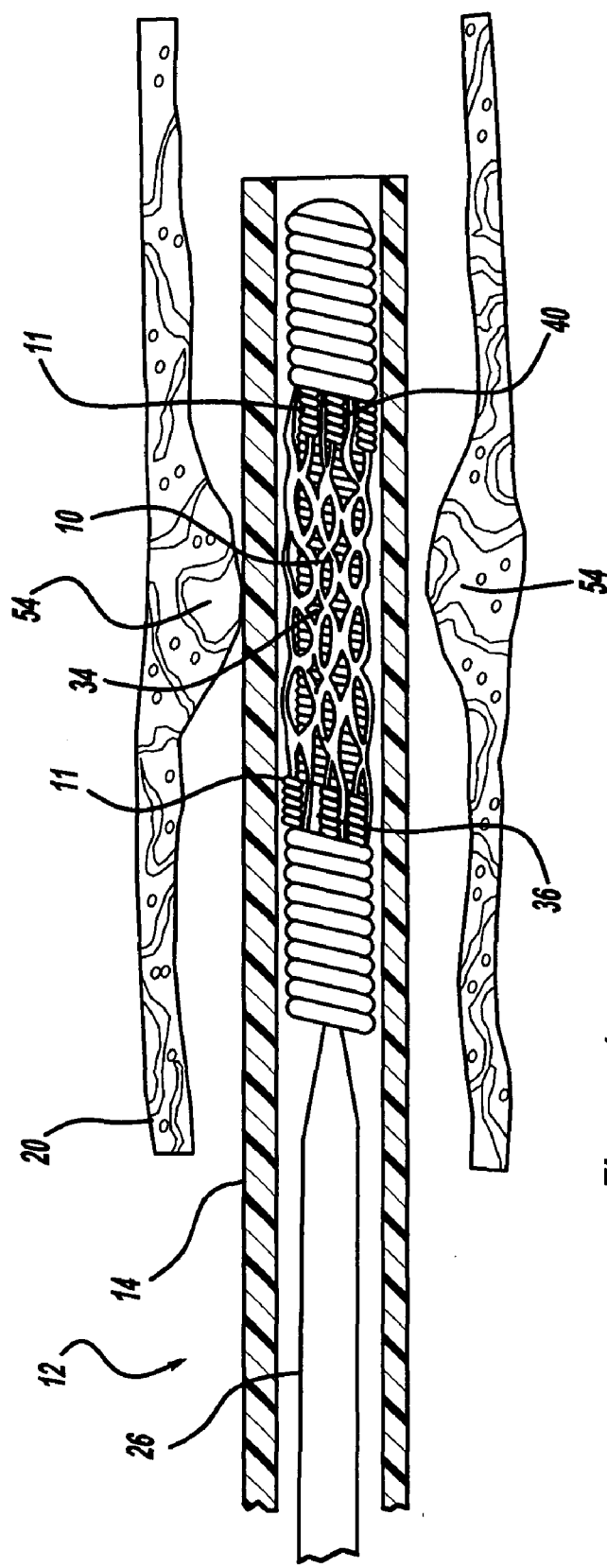
FIG. 4 is an enlarged partial sectional view of the expandable stent and delivery system disposed within a blood vessel of the body and aligned adjacent to a blockage within the vessel.

FIG. 4 illustrates the expandable stent 10 and delivery system 12 positioned within a blood vessel 20 within the brain. Initially, the stent 10 is anchored to the core member 26 by mounting the stent on the intermediate cylindrical member 34 and aligning and setting the anchor members 11 within the first and second gaps 36, 40. The core member 26 is then slid into the deployment catheter 14 to thereby hold the stent 10 in its constrained configuration. Then, the delivery system 12 is inserted into the blood vessel 20 and advanced distally until the stent 10 is aligned with the blockage area 54.

FIG. 5 shows the deployment catheter 14 moved proximally, releasing anchor members 11 on the distal strut members 46 from the second gap 40 and allowing the distal section 50 of the expandable stent 10 to begin expanding. During expansion, the distal section 50 of the stent 10 comes in contact with the wall of the blood vessel 20.

As illustrated in FIG. 6, the deployment catheter 14 is again moved proximally, releasing the anchor members 11 on the proximal strut members 44 from the first gap 36 and allowing the proximal section 48 of the stent 10 to expand. Once the stent 10 is fully deployed within the blood vessel 20, the core member 26 remains extended through the stent 10 and thus acts as a guide wire, providing a physician with easier access to locations within the blood vessel distal of the stent.

If, during the deployment process, it is determined that the stent 10 should be relocated or realigned, the deployment catheter 14 may be used to resheath the stent 10. With the stent 10 positioned on the core member 26 as described above, if the deployment catheter 14 is not withdrawn beyond the anchor members 11 on the proximal strut members 44, the stent will remain interlocked on the core member 26. In this configuration, the stent 10 may be resheathed. To resheath the stent 10, the deployment catheter 14 is moved distally forcing the stent back onto the intermediate cylindrical member 34, compressing the distal section 50 of the stent, and forcing the anchor members 11 on the distal strut members 46 to become interlocked within the second gap 40. The stent 10 and delivery system 12 may then be withdrawn or repositioned to a different location within the blood vessel 20.

Figure 7:
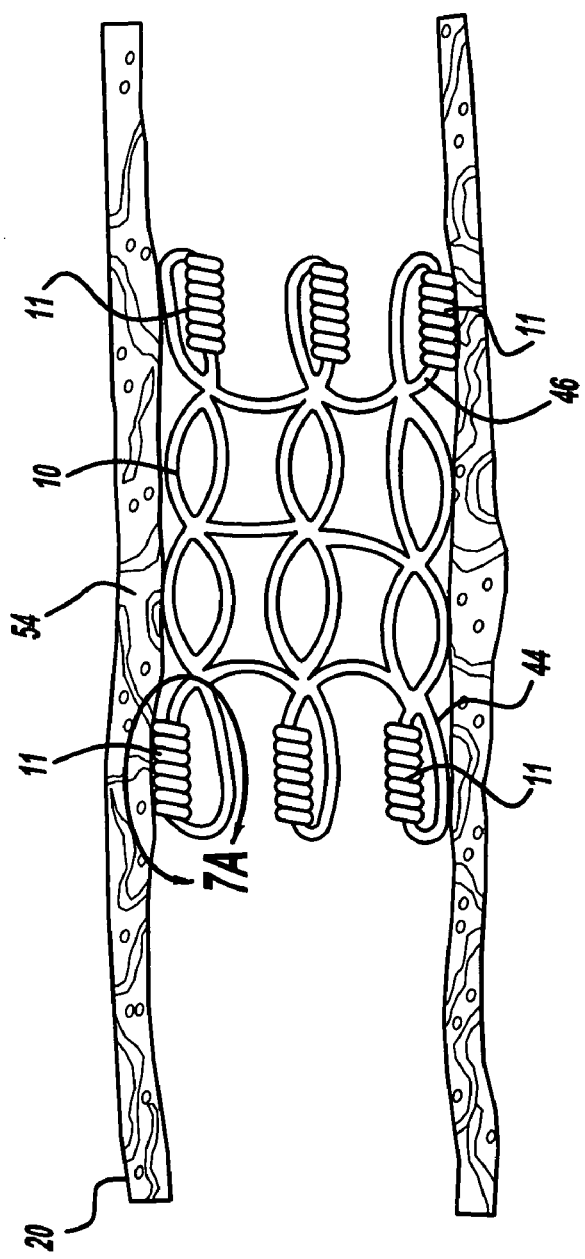
FIG. 7 is an enlarged sectional view of the expandable stent expanded within the blood vessel after the delivery system has been withdrawn from the blood vessel.

FIG. 7 illustrates the expandable stent 10 fully expanded within the blood vessel 20. As shown, the delivery system 12 has been removed from the blood vessel 20. The expanding force of the stent 10 pushes the blockage area 54 radially outward, thereby opening the blood vessel 20 and thus allowing for greater blood flow.

Figure 7B:
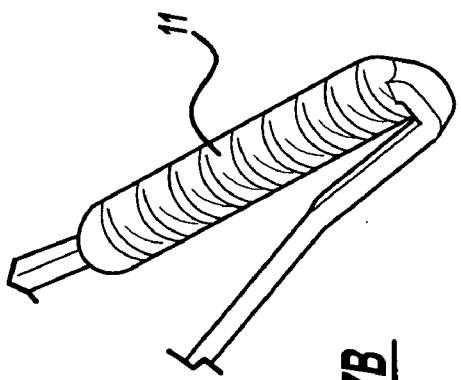
FIG. 7B is an enlarged view of the anchor member.
Figure 7A:
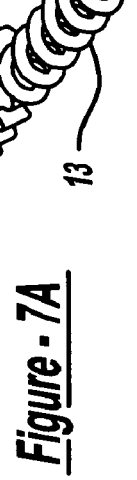
FIG. 7A is an enlarged sectional view of a coil, formed of radiopaque material, being wound onto a threaded portion of a strut member to form an anchor member.

FIGS. 7A and 7B illustrate the threaded portion 15 of a strut member 46/44 and a radiopaque coil 13. The threaded portion 15 is preferably formed by cutting threads into two opposing edges of a strut member 46/44 when the stent is laser cut from a nitinol tubular member. Alternatively, threads may be cut on only one edge of the strut member or a heat-molding technique may be used to form the threaded portion 15 on the strut member 46/44. The radiopaque coil 13, which is formed of a metallic or polymeric material which exhibits the characteristic of being radiopaque, is preferably formed of tantalum or tantalum alloy. The radiopaque coil may also be comprised of gold, gold alloy, platinum, platinum alloy, titanium, zirconium, bromine, iodine, barium, bismuth, or any combination thereof.

The radiopaque coil 13 is wound onto the threaded portion 15 to thereby form an anchor member 11, as illustrated in FIG. 7B. The radiopaque coil 13 is preferably secured to the threaded portion 15 using an adhesive material, such as a UV adhesive which is thermally cured. The anchor member 11 has an outer diameter between 0.002 inches and 0.100 inches, preferably 0.008 inches, and is between 0.019 inches and 0.190 inches long, preferably 0.040 inches with a length less than the length of the gaps 36, 40. In addition to being used to interlock the stent 10 to the core member 26, the anchor member 11 serves as a radiopaque marker for improved visualization during the deployment of the stent within the blood vessel 20. In an alternative embodiment, the threaded portion 15 may be formed such that the teeth of the threaded portion are spaced apart to provide sufficient room for turns from two interlocked radiopaque coils. With this spacing, two radiopaque coils may be wound together onto the threaded portion 15.

Figure 8:
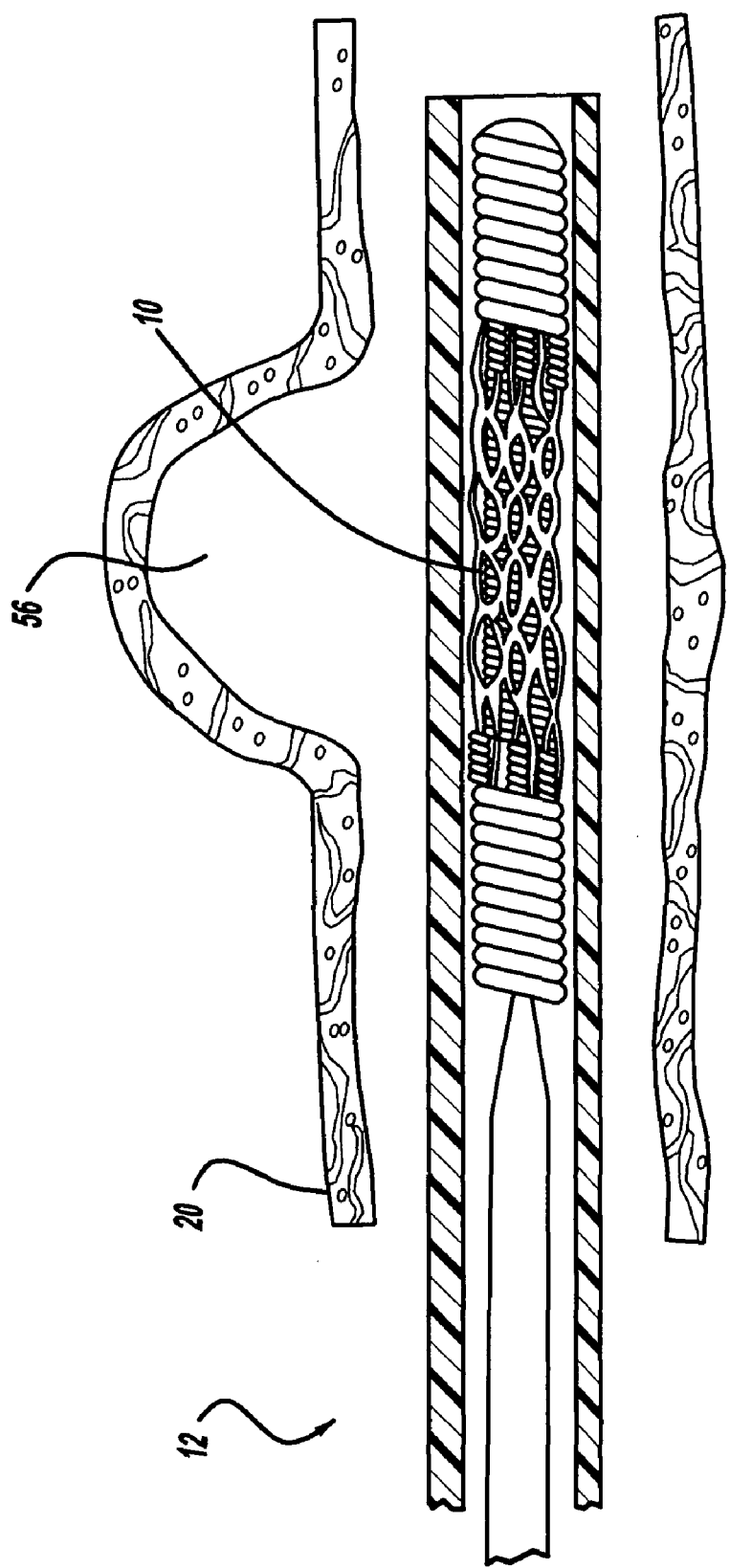
FIG. 8 is an enlarged partial sectional view of the expandable stent and delivery system disposed within a blood vessel and aligned adjacent to an aneurysm.

FIG. 8 illustrates the expandable stent 10 and delivery system 12 aligned with an aneurysm 56 within a blood vessel 20 of the brain. From this configuration, the stent 10 may be deployed and used to cover the aneurysm 56.

Figure 9:
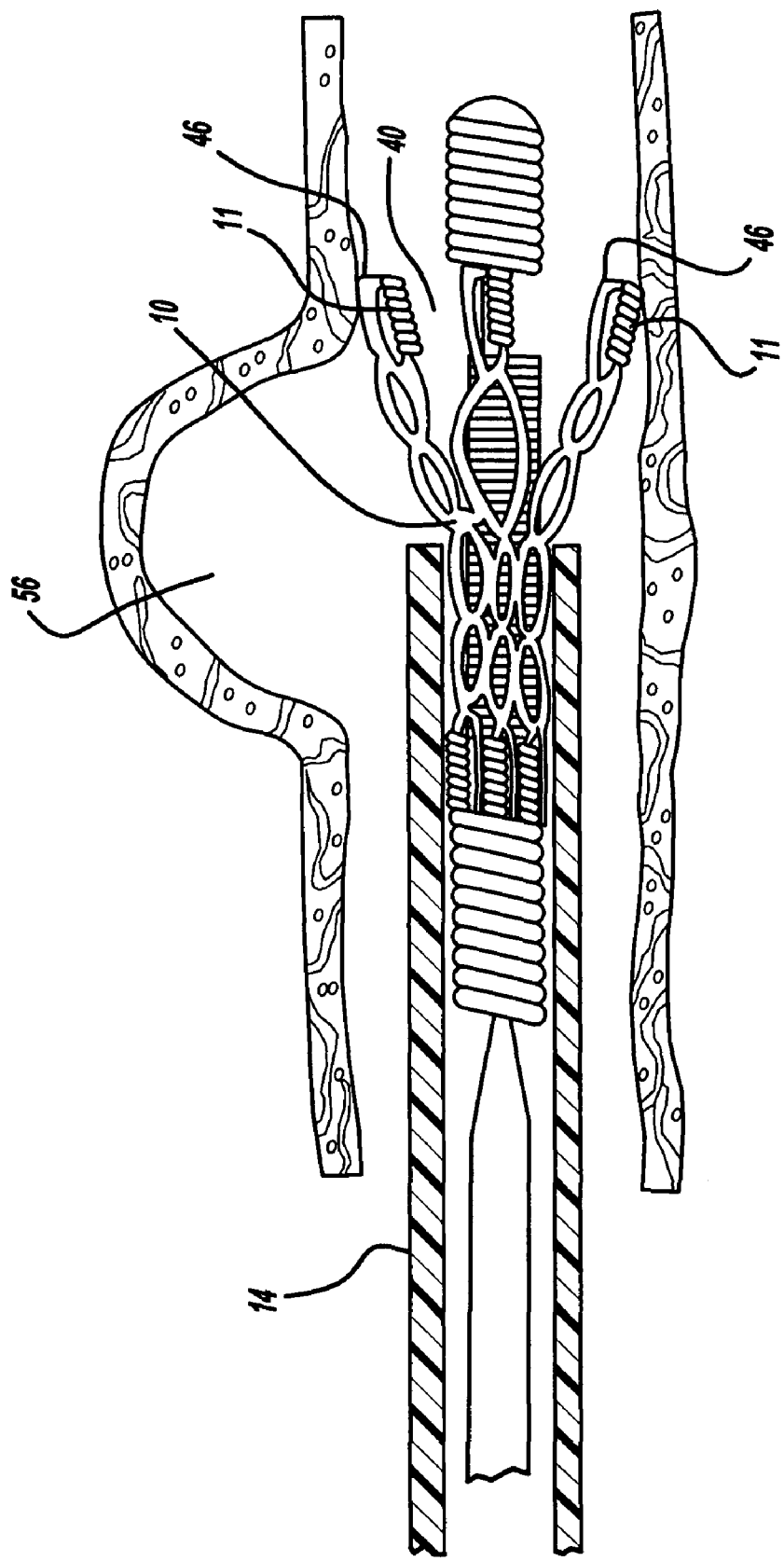
FIG. 9 is an enlarged partial sectional view of the delivery system with the deployment catheter moved proximally, allowing the distal section of the expandable stent to expand within the blood vessel while the proximal section of the expandable stent remains interlocked onto the deployment catheter.

As shown in FIG. 9, in order to deploy the expandable stent 10, the deployment catheter 14 is moved proximally, allowing the anchor members 11 on the distal strut members 46 to exit the second gap 40. The expandable stent 10 is thus allowed to partially deploy and to begin covering the aneurysm 56.

Figure 10:
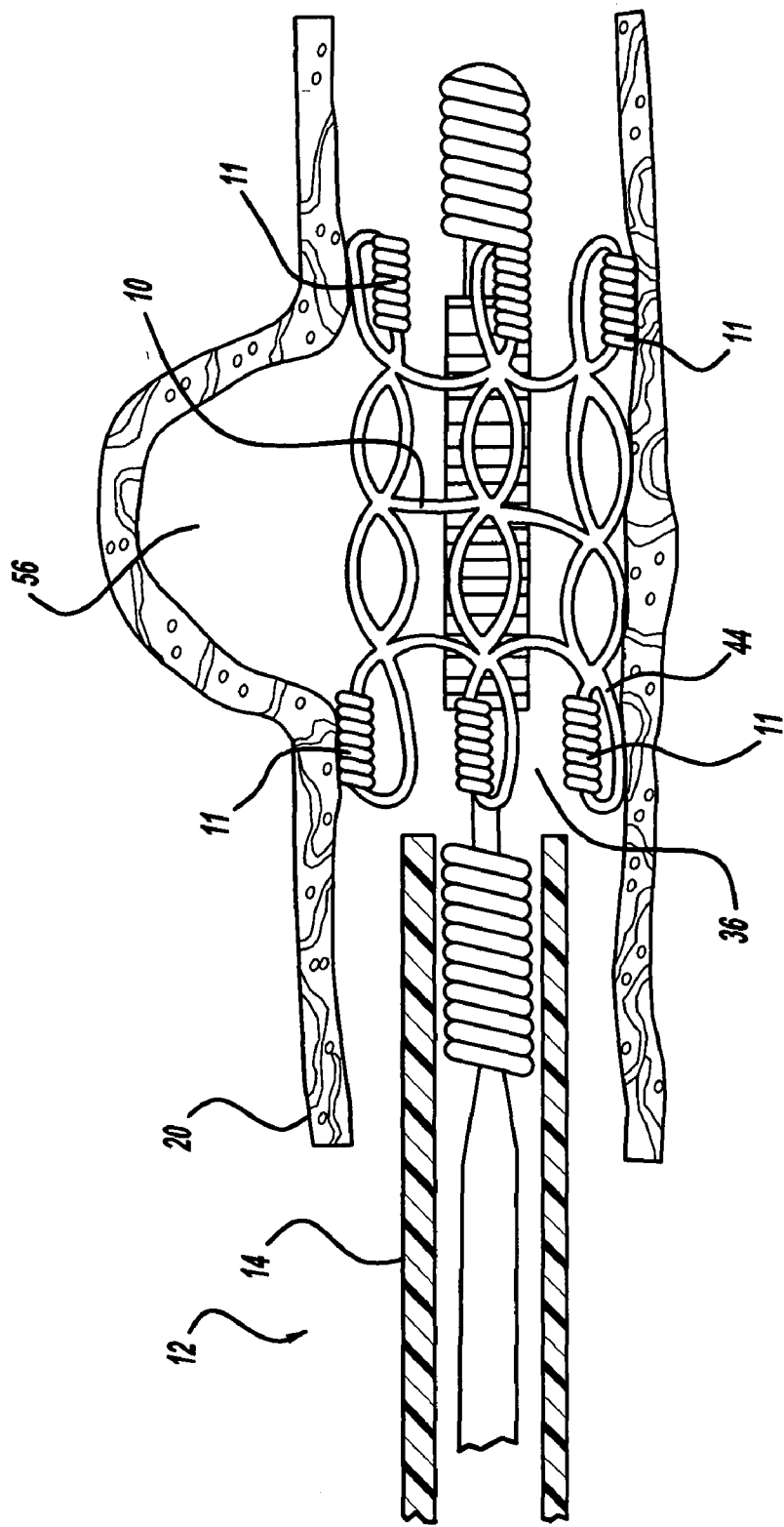
FIG. 10 is an enlarged sectional view of the delivery system with the deployment catheter moved proximally, allowing the expandable stent to fully expand within the blood vessel and thus provide a cover for the aneurysm.

FIG. 10 illustrates the stent 10 fully deployed within the blood vessel 20 and the delivery system 12 still within the vessel 20. The deployment catheter 14 is moved proximally causing the anchor members 11 on the proximal strut members 44 to exit the first gap 36 thereby allowing the stent 10 to be fully deployed and to cover the aneurysm 56.

Figure 11:
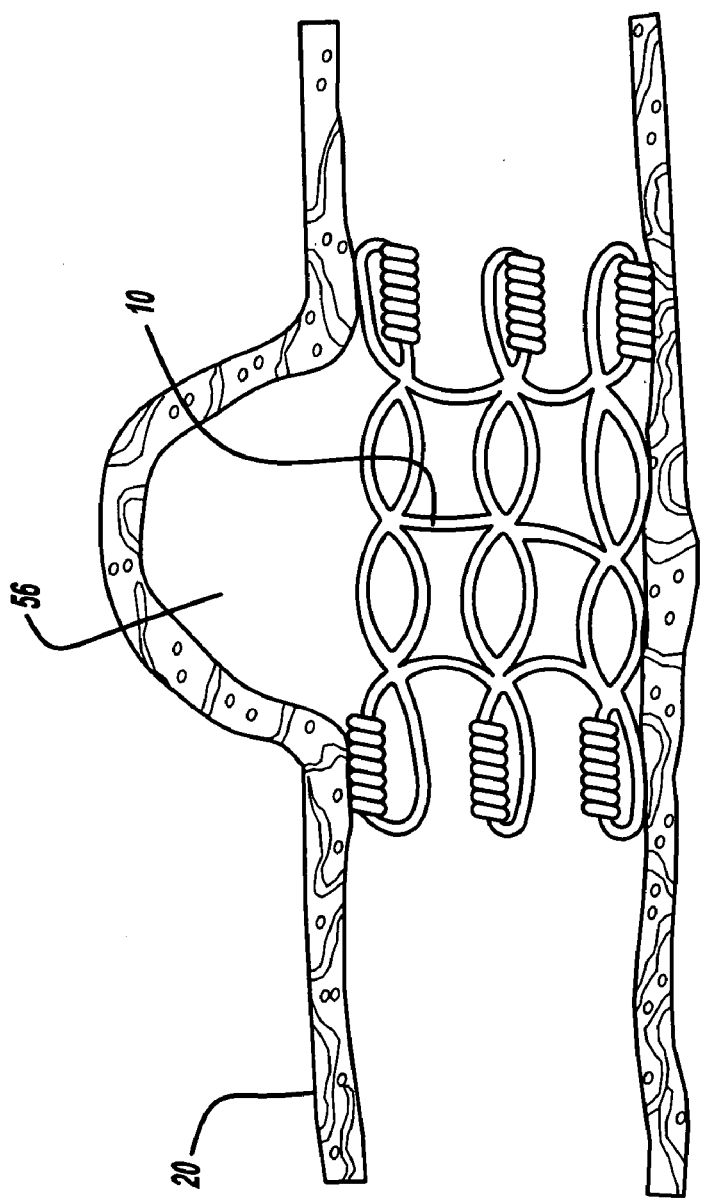
FIG. 11 is an enlarged sectional view of the expandable stent fully expanded within the blood vessel and covering the aneurysm after the delivery system has been removed from the blood vessel.

FIG. 11 illustrates the expandable stent 10 deployed within the blood vessel 20 after the delivery system 12 has been removed from the blood vessel. The stent 10 covers the aneurysm 56.

Figure 12:
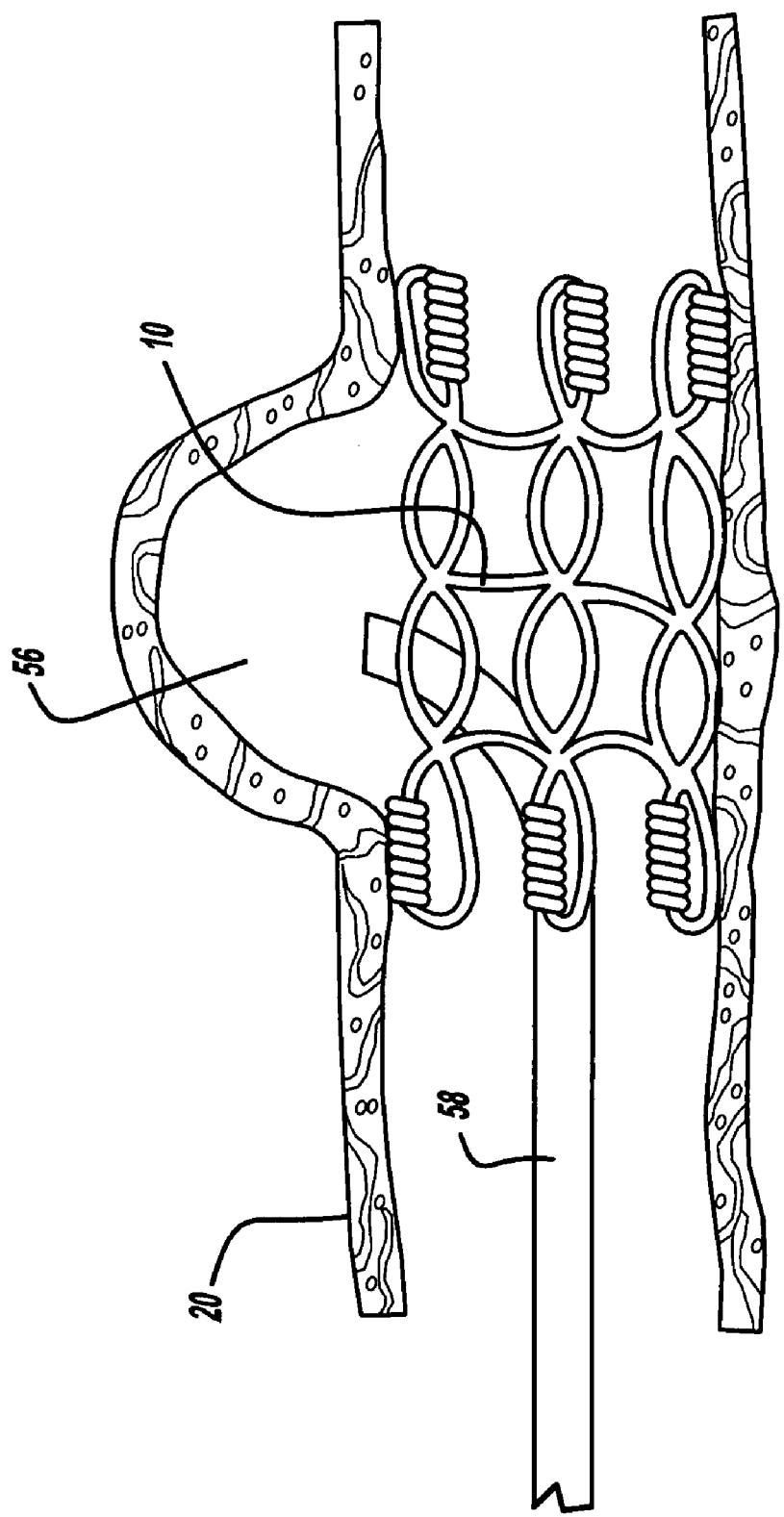
FIG. 12 is an enlarged sectional view of the expandable stent within the blood vessel with a microcatheter inserted through the wall of the stent and into the aneurysm in order to place coils within the aneurysm.

FIG. 12 shows the expandable stent 10 deployed within the blood vessel 20 with a microcatheter 58 inserted into the blood vessel 20, through the wall of the stent 10, and into the aneurysm 56. In this position, embolic agents and medical devices may be delivered into the aneurysm 56.

Figure 13:
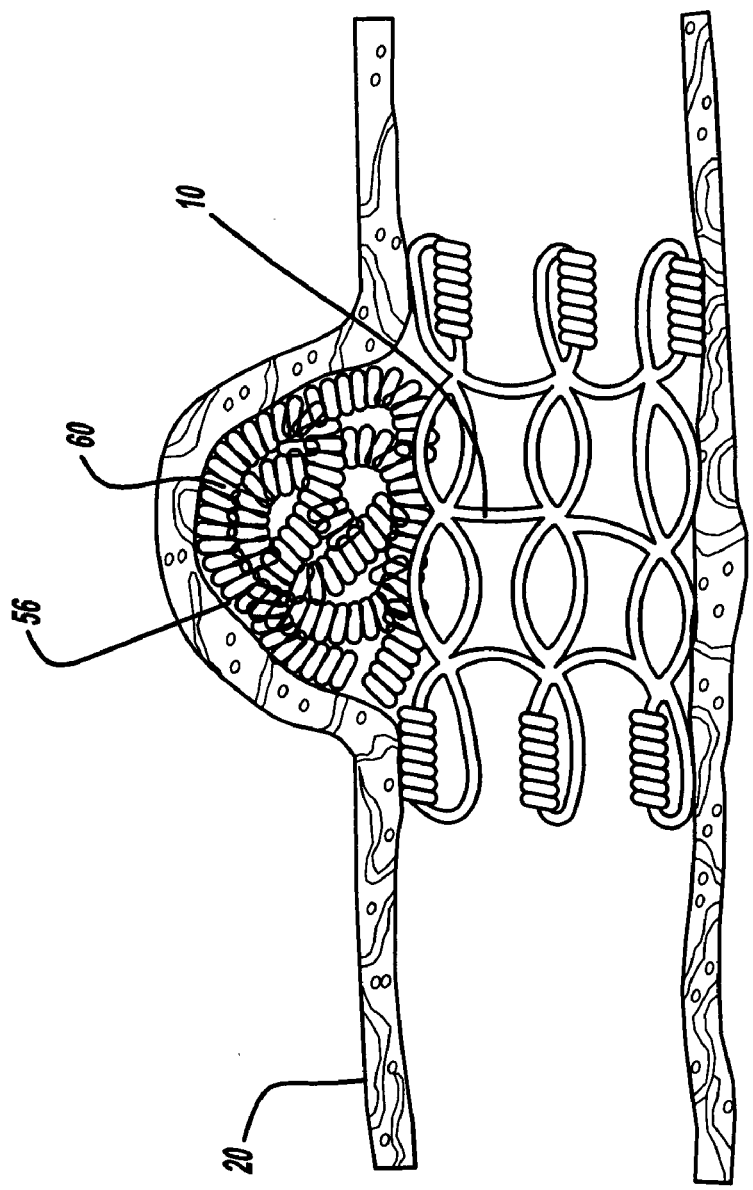
FIG. 13 is an enlarged sectional view of the expandable stent within the blood vessel and covering the aneurysm with an embolic coil placed within the aneurysm; and, FIG. 14 is an enlarged detailed view of the expandable stent.

FIG. 13 shows the expandable stent 10 deployed within the blood vessel 20 and covering the aneurysm 56. An embolic coil 60 is placed within the aneurysm 56 and is confined within the aneurysm 56 by the stent 10.

Figure 14:
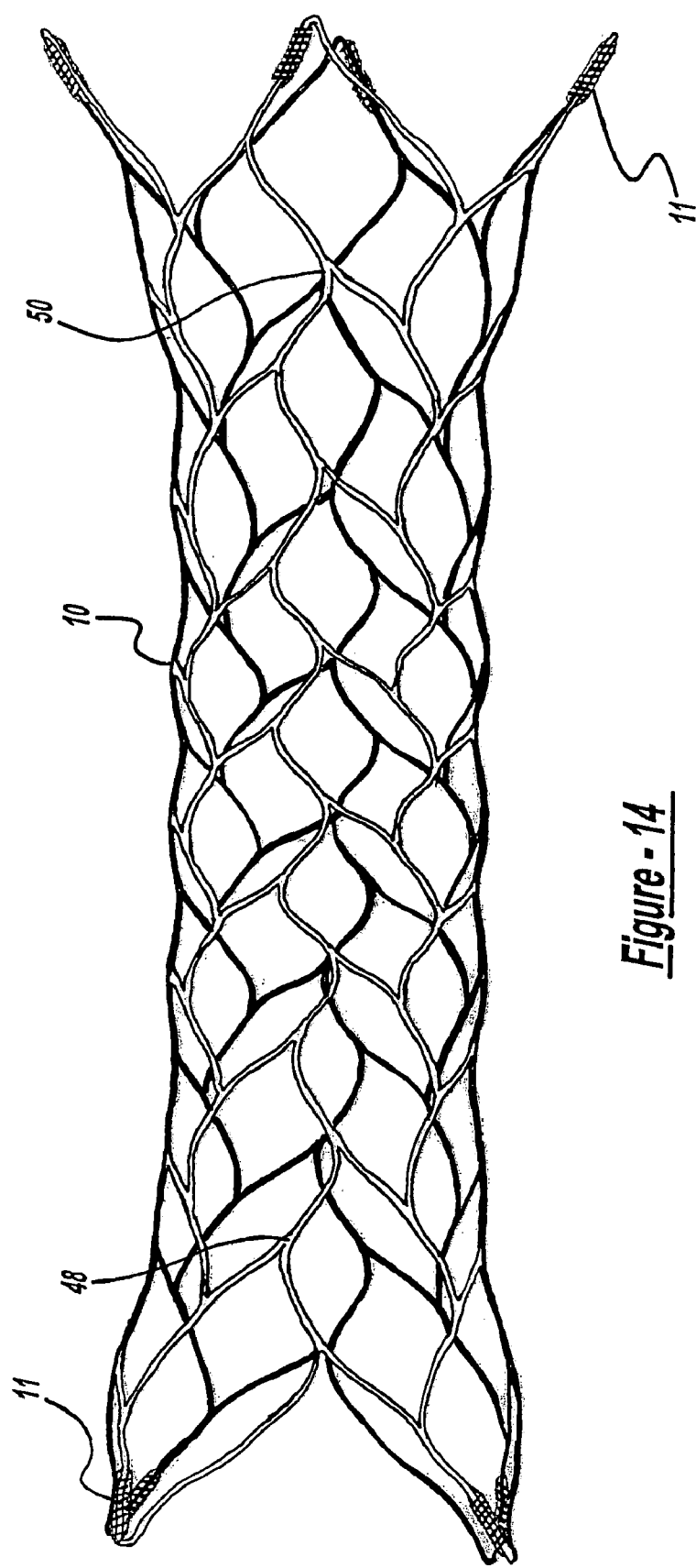

FIG. 14 illustrates the expandable stent 10 in more detail. Preferably, the proximal and distal sections 48, 50 of the stent 10 are flared to produce outer diameters at the proximal and distal ends greater than the outer diameter of the central section of the stent. Flaring of the proximal and the distal sections 48, 50 of the stent 10 is incorporated into the stent design so that the stent conforms to the blood vessel 20. The flared ends of the stent 10 press against the wall of the blood vessel to secure the stent to the blood vessel. The flaring of the proximal distal sections 48, 50 of the stent 10 is accomplished by laser-cutting the stent so that the cells in the proximal and distal sections of the stent are of an elongated configuration. Then, the stent 10 is heat-treated with the proximal and distal sections 48, 50 of the stent constrained into the appropriate flared configuration. Preferably, the proximal and distal sections 48, 50 of the stent 10 are flared to produce outer diameters of twice the outer diameter of the central section of the stent 10. The stent 10 is then heat-treated so that it becomes "self-expanding."

As illustrated in FIG. 14, the stent 10 preferably includes eight anchor members 11. The anchor members are preferably positioned within the proximal and distal sections 48, 50 of the stent 10. Anchor members 11 may alternatively be positioned within the central section of the stent 10.

Although a preferred embodiment of the present invention has been described, it is to be understood that various modifications may be made by those skilled in the art without departing from the scope of the claims which follow.

That which is claimed is:

1. An expandable stent and stent delivery system comprising:
    a delivery system including an elongated core member having a distal portion, a proximal cylindrical member disposed about the distal portion of said elongated core member, and a distal cylindrical member disposed about the distal portion of said elongated core member and generally positioned distally from said proximal cylindrical member and spaced apart from said proximal cylindrical member to define a gap having a longitudinal length;
    an expandable stent comprising a small diameter skeletal tubular member having a thin wall, said wall of said tubular member is cut to define a plurality of cells which are formed by a plurality of interconnected strut members, a first one of said plurality of strut members being formed with a threaded portion on said first strut member, a coil formed of radiopaque material being wound onto said threaded portion of said first strut member to thereby define an anchor member, said anchor member having a longitudinal length no greater than the longitudinal length of said gap, and said expandable stent being mounted on at least one cylindrical member and positioned such that said anchor member is disposed within said gap; and,
    a deployment catheter having a lumen extending therethrough and disposed about said elongated core member such that said deployment catheter compresses said expandable stent about at least one cylindrical member causing said anchor member to be retained in said gap and thereby causing said expandable stent to be interlocked onto said elongated core member.

2. An expandable stent and stent delivery system as defined in claim 1, in which a second one of said plurality of strut members is formed to create a threaded portion and a coil formed of radiopaque material is wound onto said threaded portion of said second strut member to thereby define a second anchor member.

3. An expandable stent and stent delivery system as defined in claim 2, wherein said expandable stent includes a distal section and one anchor member is positioned within the distal section of said expandable stent.

4. An expandable stent and stent delivery system as defined in claim 3, wherein said expandable stent includes a proximal section and one anchor member is positioned within the proximal section of said expandable stent.

5. An expandable stent and stent delivery system as defined in claim 2, wherein said expandable stent includes a central section, a flared proximal section, and a flared distal section, and wherein said flared proximal section and said flared distal section have outer diameters greater than the outer diameter of the central section of said expandable stent.

6. An expandable stent and stent delivery system comprising:
    a delivery system including an elongated core member having a distal portion, a proximal cylindrical member disposed about the distal portion of said elongated core member, and a distal cylindrical member disposed about the distal portion of said elongated core member and generally positioned distally from said proximal cylindrical member and spaced apart from said proximal cylindrical member to define a gap having a longitudinal length;
    an expandable stent comprising a small diameter skeletal tubular member having a thin wall, said wall of said tubular member being cut to define a plurality of cells which are formed by a plurality of interconnected strut members, a first one of said plurality of strut members having threads cut into an edge of said first strut member, a coil formed of radiopaque material being wound onto said threads of said first strut member to thereby define an anchor member, said anchor member having a longitudinal length no greater than the longitudinal length of said gap, and said expandable stent being mounted on at least one cylindrical member and positioned such that said anchor member is disposed within said gap; and,
    a deployment catheter having a lumen extending therethrough and disposed about said elongated core member such that said deployment catheter compresses said expandable stent about at least one cylindrical member causing said anchor member to be retained in said gap and thereby causing said expandable stent to be interlocked onto said elongated core member.

7. An expandable stent and stent delivery system as defined in claim 6, wherein said first strut member includes threads cut into two opposing edges and a coil formed of radiopaque material being wound into said threads of said first strut member to thereby define a first anchor member.

8. An expandable stent and stent delivery system as defined in claim 7, in which a second one of said plurality of strut members includes threads cut into two opposing edges of said second strut member, and a coil formed of radiopaque material is wound onto said threads of said second strut member to thereby define a second anchor member.

9. An expandable stent and stent delivery system as defined in claim 8, wherein said expandable stent includes a distal section and one anchor member is positioned within the distal section of said expandable stent.

10. An expandable stent and stent delivery system as defined in claim 9, wherein said expandable stent includes a proximal section and one anchor member is positioned within the proximal section of said expandable stent.

11. An expandable stent and stent delivery system as defined in claim 8, wherein said expandable stent includes a central section, a flared proximal section, and a flared distal section, and wherein said flared proximal section and said flared distal section have outer diameters greater than the outer diameter of the central section of said expandable stent.

12. An expandable stent comprising:
a small diameter skeletal tubular member having a thin wall;
said wall of said tubular member including a plurality of cells which are formed by a plurality of interconnected strut members, a first one of said plurality of strut members being formed with a threaded portion on said first strut member; and,
a radiopaque marker, which takes the form of a coil formed of radiopaque material being wound onto said threaded portion of said first strut member.

13. An expandable stent as defined in claim 12, wherein said tubular member includes a distal section and said radiopaque marker is positioned within the distal section of said tubular member.

14. An expandable stent as defined in claim 12, wherein said tubular member includes a proximal section and said radiopaque marker is positioned within the proximal section of said tubular member.

15. An expandable stent as defined in claim 12, in which a second one of said plurality of strut members is formed to create a threaded portion on said second strut member and said second strut member includes a radiopaque marker, which take the form of a coil formed of radiopaque material being wound onto said threaded portion of said second strut member.

16. An expandable stent as defined in claim 15, wherein said tubular member includes a distal section and one radiopaque marker is positioned within the distal section of said tubular member.

17. An expandable stent as defined in claim 16, wherein said tubular member includes a proximal section and one radiopaque marker is positioned within the proximal section of said tubular member.

18. An expandable stent as defined in claim 15, wherein said tubular member includes a central section, a flared proximal section, and a flared distal section, and wherein said flared proximal section and said flared distal section have outer diameters greater than the outer diameter of the central section of said tubular member.

19. An expandable stent as defined in claim 15, wherein said tubular member includes a central section, a flared proximal section, and a flared distal section, and wherein said flared proximal section and said flared distal section have outer diameters between two and three times the outer diameter of the central section of said tubular member.

20. An expandable stent as defined in claim 15, wherein said tubular member includes a central section, a flared proximal section, and a flared distal section, and wherein said flared proximal section and said flared distal section have outer diameters approximately equal to three times the outer diameter of the central section of said tubular member.

21. An expandable stent as defined in claim 12, wherein said tubular member includes a central section, a flared proximal section, and a flared distal section, and wherein said flared proximal section and said flared distal section have outer diameters greater than the outer diameter of the central section of said tubular member.

22. An expandable stent as defined in claim 12, wherein said tubular member includes a central section, a flared proximal section, and a flared distal section, and wherein said flared proximal section and said flared distal section have outer diameters between two and three times the outer diameter of the central section of said tubular member.

23. An expandable stent as defined in claim 12, wherein said tubular member includes a central section, a flared proximal section, and a flared distal section, and wherein said flared proximal section and said flared distal section have outer diameters approximately equal to three times the outer diameter of the central section of said tubular member.

24. An expandable stent comprising:
a small diameter skeletal tubular member having a thin wall;
said wall of said tubular member including a plurality of cells which are formed by a plurality of interconnected strut members, eight of said plurality of strut members being formed with a threaded portion on each of said eight strut members; and,
eight radiopaque markers, which take the form of a coil formed of radiopaque material being wound onto each threaded portion of said eight strut members.

25. An expandable stent as defined in claim 24, wherein said tubular member includes a distal section and one radiopaque marker is positioned within the distal section of said tubular member.

26. An expandable stent as defined in claim 25, wherein said tubular member includes a proximal section and one radiopaque marker is positioned within the proximal section of said tubular member.

27. An expandable stent comprising:
a small diameter skeletal tubular member having a thin wall;
said wall of said tubular member being cut to define a plurality of cells which are formed by a plurality of interconnected strut members, a first one of said plurality of strut members having threads cut into an edge of said first strut member; and
a coil formed of radiopaque material being wound onto said threads of said first strut member.

28. An expandable stent as defined in claim 27, wherein said tubular member includes threads cut into two opposing edges of said first strut member and a radiopaque marker, which takes the form of a coil formed of radiopaque material being wound onto said threads of said first strut member.

29. An expandable stent as defined in claim 28, wherein said tubular member includes a distal section and said radiopaque marker is positioned within the distal section of said tubular member.

30. An expandable stent as defined in claim 28, wherein said tubular member includes a proximal section and said radiopaque marker is positioned within the proximal section of said tubular member.

31. An expandable stent as defined in claim 28, wherein said tubular member includes a second one of said plurality of strut members having threads cut into two opposing edges of said second strut member and having a radiopaque marker, which take the form of a coil formed of radiopaque material being wound onto said threads of said second strut member.

32. An expandable stent as defined in claim 31, wherein said tubular member includes a distal section and one radiopaque marker is positioned within the distal section of said tubular member.

33. An expandable stent as defined in claim 32, wherein said tubular member includes a proximal section and one radiopaque marker is positioned within the proximal section of said tubular member.

34. An expandable stent as defined in claim 31, wherein said tubular member includes a central section, a flared proximal section, and a flared distal section, and wherein said flared proximal section and said flared distal section have outer diameters greater than the outer diameter of the central section of said tubular member.

35. An expandable stent as defined in claim 31, wherein said tubular member includes a central section, a flared proximal section, and a flared distal section, and wherein said flared proximal section and said flared distal section have outer diameters between two and three times the outer diameter of the central section of said tubular member.

36. An expandable stent as defined in claim 31, wherein said tubular member includes a central section, a flared proximal section, and a flared distal section, and wherein said flared proximal section and said flared distal section have outer diameters approximately equal to three times the outer diameter of the central section of said tubular member.

37. An expandable stent as defined in claim 28, wherein said tubular member includes a central section, a flared proximal section, and a flared distal section, and wherein said flared proximal section and said flared distal section have outer diameters greater than the outer diameter of the central section of said tubular member.

38. An expandable stent as defined in claim 28, wherein said tubular member includes a central section, a flared proximal section, and a flared distal section, and wherein said flared proximal section and said flared distal section have outer diameters between two and three times the outer diameter of the central section of said tubular member.

39. An expandable stent as defined in claim 28, wherein said tubular member includes a central section, a flared proximal section, and a flared distal section, and wherein said flared proximal section and said flared distal section have outer diameters approximately equal to three times the outer diameter of the central section of said tubular member.

40. An expandable stent comprising:
a small diameter skeletal tubular member having a thin wall;
said wall of said tubular member being cut to define a plurality of cells which are formed by a plurality of interconnected strut members, eight of said plurality of strut members having threads cut into two opposing edges of said eight strut members; and
eight radiopaque markers, which take the form of a coil formed of radiopaque material being wound onto each of said threads of said eight strut members.

41. An expandable stent as defined in claim 40, wherein said tubular member includes a distal section and one of said eight radiopaque markers is positioned within the distal section of said tubular member.

42. An expandable stent as defined in claim 41, wherein said tubular member includes a proximal section and one of said eight radiopaque markers is positioned within the proximal section of said tubular member.

* * * * *